United States Patent [19]

Schmidhammer et al.

[11] Patent Number: 4,540,837

[45] Date of Patent: Sep. 10, 1985

[54] PROCESS FOR THE WORK-UP OF RESIDUES OF CHLORINATION

[75] Inventors: Ludwig Schmidhammer, Haiming; Gerhard Dummer, Burgkirchen; Klaus Haselwarter; Rudolf Strasser, both of Burghausen, all of Fed. Rep. of Germany

[73] Assignee: Wacker-Chemie GmbH, Munich, Fed. Rep. of Germany

[21] Appl. No.: 519,969

[22] Filed: Aug. 3, 1983

[30] Foreign Application Priority Data

Sep. 10, 1982 [DE] Fed. Rep. of Germany ....... 3233640
Sep. 30, 1982 [DE] Fed. Rep. of Germany ....... 3236323

[51] Int. Cl.$^3$ .............................................. C07C 17/38
[52] U.S. Cl. .................................................... 570/211
[58] Field of Search ........................ 570/211, 238, 262

[56] References Cited

U.S. PATENT DOCUMENTS

| | | | |
|---|---|---|---|
| 2,321,472 | 6/1943 | Engs et al. | 570/238 |
| 3,647,894 | 3/1972 | Jackson et al. | 570/211 |
| 3,803,005 | 4/1974 | Miserlis et al. | 570/262 |
| 3,992,460 | 11/1976 | Tsao | 570/238 |
| 4,031,149 | 6/1977 | Eden | 570/238 |
| 4,307,261 | 12/1981 | Beard et al. | 570/262 |

FOREIGN PATENT DOCUMENTS

| | | | |
|---|---|---|---|
| 2205640 | 8/1973 | Fed. Rep. of Germany | 570/238 |

*Primary Examiner*—Charles F. Warren
*Assistant Examiner*—Joseph A. Boska
*Attorney, Agent, or Firm*—Collard, Roe & Galgano

[57] ABSTRACT

A process for the work-up of chlorination residues by dissolving the same at temperatures between 100° and 180° C. in chlorine- and oxygen-containing hydrocarbons having a ratio by weight of hydrogen to chlorine of 0.028–0.06:1, a ratio by weight of oxygen:carbon of 0.0038–0.0089:1, and an atomic ratio of carbon:hydrogen of 1:1.1–1.9 and/or in hydrocarbons, boiling between 160° and 380° C. at one bar abs. and having an atomic ratio carbon:hydrogen of 1:1.85–2.0 so as to obtain a liquid preparation having a ratio by weight of hydrogen:chlorine of 0.028–0.05:1.

7 Claims, No Drawings

PROCESS FOR THE WORK-UP OF RESIDUES OF CHLORINATION

The invention relates to a process for the work-up of residues of chlorination.

Particularly in chlorination at high temperatures, e.g., such as used in the preparation of carbon tetrachloride and/or perchloroethylene, from $C_1$ to $C_3$ hydrocarbons, or from partly chlorinated hydrocarbons having 1 to 4 carbon atoms, undesirable mixtures are obtained as residues, which contain substantially perchlorinated compounds, especially hexachlorobenzene, as well as hexachloroethane and hexachlorobutadiene.

For reasons of environmental protection, as well as for economical and technical considerations, it is an important problem to render these residues harmless and innocuous. Hexachlorobenzene, which is the main component of these residues, is persistent and would, when diffused into the environment, become enriched by bio-accumulation. The residues are, therefore, frequently dumped in underground sites assigned by governmental authorities. This method is, however, unsatisfactory, among other reasons, because 5–20% by weight of the chlorine used is lost, depending on the manner in which the chlorination process was carried out.

On the other hand, rendering the residues harmless by burning, if possible while recovering the chlorine portion, presents considerable technical difficulties. It presupposes an easily measurable or dosable state of the residues, which means the residues have to be capable of flowing. Melts are only obtained at temperatures above about 230° C. They are very corrosive and difficult to handle because of their high melting points. When attempts are made to dissolve the residues, there are narrow limits within which to work, because a work-up of this type is only reasonable, if the product of combustion yields, in addition to the desired hydrogen chloride, only moderate amounts of water, because otherwise this would result only in the formation of hydrochloric acid of comparatively low value. Also, undesirable combustion by-products are formed, e.g., high amounts of carbon dioxide, carbon monoxide, and especially soot, and they would make this method of rendering harmless the residues by combustion quite uneconomical.

Another drawback is the low solubility of these chlorination residues. For instance, in benzene, only about 7.5% by weight of a residue of the typical composition of about two-thirds of hexachlorobenzene and one-quarter of hexachlorobutadiene is soluble, which would otherwise be suitable in view of its chemical constitution. In 1,2-dichloroethane, only about 1% by weight is soluble.

It is the object of the present invention to provide a process for the work-up of residues of chlorination, wherein the residues of chlorination are rendered fluid at temperatures more moderate than those necessary for melting the residues.

It is a further object to provide mixtures which can be burned in a manner that makes it possible to take care of the protection of the environment and to obtain at least the main amount of chlorine as dry hydrogen chlorine, e.g., useful for oxychlorination, while keeping expenses at a reasonable level.

Other objects and advantages will be understood from the following detailed description.

It has now been found that tar-like hydrocarbons which are obtained as by-products in the pyrolysis of dichloroethane to monomeric vinyl chloride and in the work-up of the pyrolysis products, or of crude 1,2-dichloroethane from the direct and/or oxychlorination of ethylene, may be used as solvents with satisfactory results. Alternative solvents are hydrocarbons low in aromatics of a boiling range from 160° to 300° C.

The invention is characterized by the step of dissolving chlorination residues at temperatures from 100° to 180° C. in hydrocarbons containing chlorine and oxygen, in which the following ratios by weight are present:

Hydrogen:Chlorine 0.028–0.06:1

Oxygen:Carbon 0.0038–0.0089:1 and an atomic ratio

Carbon:Hydrogen 1:1.1–1.9 and/or hydrocarbons, which have a boiling point of 160°–380° C. at one bar abs. and have an atomic ratio carbon to hydrogen 1:1.85–2.0. The amounts to be taken should yield a liquid composition in which the ratio by weight of hydrogen:chlorine is 0.028–0.05:1.

Preferably, the amount of chlorine residues in the composition is 20–50% by weight.

It is further advantageous to adjust the temperature during the work-up so that it corresponds to the following equation $$t = \frac{x + 55}{0.66} \pm 5$$

wherein t is the temperature in °C. and x represents the amount of chlorination residues indicated in % by weight calculated on the total weight of the composition.

The corrective factor ±5 represents the tolerance limit of the optimal temperature course.

Furthermore, the ratio hydrogen:chlorine in the composition is preferably 0.028 to 0.04:1.

The work-up is carried out in the technically reasonable range from 1.2 to 5.0 bar abs. If desirable, higher pressures can also be used.

The residues to be worked up according to the invention are undesirable by-products which are obtained in chlorination processes, particularly high-temperature chlorinations, as they have been described above. They are mixtures consisting of at least 95% by weight, but in most cases 100% by weight, of perchlorinated products. The basic components are hexachlorobenzene, hexachlorobutadiene and hexachloroethane. Furthermore, a low amount of chlorinated hydrocarbons may be present in the mixture which are desirable, per se, in the chlorination process. Accordingly, these chlorination residues have a chemical composition which can be represented, in fairly good approximation, by the summation formula $$C_{5\text{-}6}Cl_{5.8\text{-}6.0}$$

Hydrogen, which could be represented in the composition according to the invention, is particularly completely absent.

As mentioned above, the hydrocarbons containing oxygen and chlorine, whose chlorination residues are worked up according to the invention, are obtained in the pyrolysis of dichloroethane and in the work-up of the pyrolysis products as well as in the work-up of crude 1,2-dichloroethane resulting from the direct and- /or oxychlorination of ethylene. They are tar-like mixtures of the composition represented by the summation formula $$C_{3.0-3.5}H_{4.0-5.5}Cl_{2.6-3.6}O_{0.01-0.02} \quad (I)$$

and $$C_{2.0-2.5}H_{3.0-3.5}Cl_{2.4-3.0}O_{0.01-0.015} \quad (II)$$

Accordingly, the chlorination residues have the following ratios by weight:
Hydrogen:Chlorine 0.028–0.06:1
Oxygen:Carbon 0.0038–0.0089:1
and an atomic ratio
Carbon:Hydrogen 1:1.1–1.9.

The tar-like compositions of formula I are obtained in the first work-up step of the pyrolysis products in which the pyrolysis products are quenched after leaving the pyrolysis furnace. The compositions with less carbon shown in formula II are obtained as distillation residues in the step in which, after separation of the low-boiling components and the desired monomeric vinyl chloride, the unreacted 1,2-dichloroethane from the pyrolysis is recovered in pure state together with crude 1,2-dichloroethane from the direct- and/or oxychlorination of ethylene.

The above mentioned tar-like mixtures frequently contain some solid substances, e.g., coke and metal chlorides. It is therefore desirable to filtrate them over heated fine filters before putting them to use according to the invention. Alternatively, the chlorination residues already prepared for the work-up may be filtered before being measured into the combustion plant.

Examples for alternatively useful hydrocarbons of the boiling range of 160°–380° C. at 1 bar abs. having an atomic ratio carbon:hydrogen 1:1.85–2.0, are kerosene as well as heavy and light heating oils with an aromatic proportion below 10% by weight.

The mentioned work-up additives may be added singly or in mixture. Since the tar-like agents are undesirable by-products of the preparation of vinyl chloride which are best disposed of by combustion, they are the preferred work-up additives. In case this preferred mode of carrying out the process of the invention is used, it is possible, e.g., for equalizing the carbon/hydrogen/chlorine balance, to add low amounts of hydrocarbons of the boiling range between 160° and 380° C.

The dissolution of the chlorination residues can be achieved in a known manner, e.g. in pressure vessels provided with agitators. It is principally unimportant, in which order the components are added. The residence time of the finishing process should preferably be limited to about 10 hours, since otherwise the reasonable range of about 5 bar abs. could be exceeded due to the pressure increases caused by the splitting off of hydrogen chloride.

The process can be carried out continuously or discontinuously.

The chlorination residues treated according to the invention can finally be introduced into a known combustion apparatus. A suitable combustion process is, e.g., described in DE-OS No. 28 27 761.

According to the process of the invention, it is possible to treat chlorination residues, especially those obtained in high-temperature chlorination processes, in such a manner that they can be burned without damage to the environment. Moreover, the chlorine content present in the residues can be recovered at least in part as useful dry hydrogen chloride, for instance by using it for oxychlorination. The process according to the invention is particularly advantageous in the chemical industry in the industrially used combined production technique, since in addition to the mentioned chlorination residues, also the tars obtained in the production of vinyl chloride can be rendered harmless.

In the following, the invention will be more fully described in a few examples and comparison examples. It should, however, be understood that these are given by way of illustration and not of limitation.

EXAMPLE 1

In a high temperature chlorination process for preparing perchloroethylene, 125 kg of residues were obtained hourly having the following composition:
2.0% by weight of perchloroethylene
4.7% by weight of hexachloroethane
23.9% by weight of hexachlorobutadiene
69.4% by weight of hexachlorobenzene These chlorination residues were obtained in a concentration device at operational conditions of 270° C. and 2.6 bar abs.; they were obtained in molten condition. They contained 22.7% by weight of carbon and 77.3% by weight of chlorine. Every 8 hours 1000 kg of the residues were poured into a transportation cart having a capacity of about 4 $m^3$ which was heated by 6 bar-steam and provided with a stirrer driven by compressed air. All parts in contact with the product were made of stainless steel.

During the removal periods of 20 minutes, the molten residues were passing into the cart through a pipe with a flow rate of 3000 kg/hour. In the pipe, 3600 kg of a liquid mixture were added to the chlorination residues, the mixture being tar-like and resulting from the vinyl chloride production; and consisting of:
28.58% by weight of carbon
3.67% by weight of hydrogen
67.64% by weight of chlorine and
0.11% by weight of oxygen.

Also added were 250 kg of a hydrocarbon of the boiling fraction 180°–220° C. with an atomic ratio carbon:hydrogen–1:1.95. The two last mentioned additives had the temperature of the environment, whereas the entire mixture was maintained at 150° C. At the end of the pouring-off process, there were 2233 kg of a total mixture in the cart, the portion of chlorination residues being 43.8% by weight. The weight ratio of hydrogen:-chlorine was 0.035:1. The pressure prevailing over the mixture was about 1.05 bar at the beginning and rose to about 2.2 bar abs. at the end of the pouring process. The end product was a solution, which formed at the same time as the components were made to flow together.

The so prepared chlorination residues could then be introduced into a combustion apparatus in readily dosable amounts.

EXAMPLE 2

The process was carried out as described in Example 1 with the following modifications:

The transportation cart was operated with 2.2 bar abs.

To 1000 kg chlorination residues of the composition described in Example 1 were added 9000 kg of a liquid tar-like mixture resulting from vinyl chloride production, at a rate of 3000 kg per hour, the composition of the tar-like mixture was the following (all percentages by weight):

24.49% carbon
2.86% hydrogen
72.45% chlorine
0.20% oxygen

After about 20 minutes a solution was obtained composed of 25% chlorination residues. The temperature of the mixture was maintained at 121° C. The ratio of hydrogen:chlorine in the mixture was 0.029:1 by weight. The pressure above the mixture rose from an initial 1 bar abs. to 3 bar abs.

The so prepared composition could then be introduced into a combustion apparatus in readily dosable amounts.

Comparison Example 1

Into a bomb tube of glass, 10 g of chlorination residues of the composition described in Example 1 were introduced together with 10 g hydrocarbon whose atomic carbon:hydrogen ratio was 1:1.33. After closing the glass bomb by melting down, the temperature was raised to 200° C. The mixture did not dissolve.

EXAMPLE 3

Into a bomb tube of glass (in analogy to Comparison Example 1), 10 g chlorination residues of the composition described in Example 1 were introduced together with 40 g of the tar-like mixture obtained in the production of vinyl chloride, also mentioned in Example 1. After melting down the bomb tube, the temperature was raised to 110° C. The chlorination residues were completely dissolved.

While only several embodiments and examples of the present invention have been described, it will be obvious to those skilled in the art that other changes and variations can be made in carrying out the present invention, without departing from the spirit and scope thereof, as defined in the appended claims.

What is claimed is:

1. A process for the work-up of chlorination residues, comprising the steps of:

obtaining a preparation containing chlorination residues composed substantially of perchlorinated compounds having a chemical composition represented approximately by the summation formula $$C_{5-6}Cl_{5.8-6.0}$$

and dissolving said chlorination residues at temperatures between 100° and 180° C. in a solvent selected from the group consisting of hydrocarbons containing chlorine and oxygen, in which the ratio of hydrogen:chlorine is 0.028–0.06:1 by weight, the ratio of oxygen:carbon is between 0.0038–0.0089:1 by weight, the atomic ration of carbon to hydrogen is from 1:1.1–1.9, hydrocarbons having a boiling point between 160° and 180° C. at one bar abs. in which the atomic ratio of carbon:hydrogen is between 1:1.85–2 and a combination of said hydrocarbons, wherein the amounts of components are so chosen that a liquid preparation is obtained having a weight ratio of hydrogen:chlorine from 0.028 to 0.05:1.

2. The process of claim 1, wherein the proportion of chlorination residues in said preparation amounts to 20–50% by weight.

3. The process of claim 1, wherein the ratio by weight of hydrogen:chlorine in said preparation is 0.028–0.04:1.

4. The process of claim 1, wherein the temperature during the work-up is so adjusted that it corresponds to the equation $$t = \frac{x + 55}{0.66} \pm 5$$

wherein t is the temperature in °C. and x is the proportion of chlorination residues, expressed in % by weight, calculated on the total weight of the preparation.

5. The process of claim 1, wherein said perchlorinated compounds are present in said chlorinated residues in an amount of at least 95% by weight.

6. The process of claim 1, wherein the perchlorinated compounds are present in said chlorination residues in an amount of 100% by weight.

7. The process of claim 1, wherein said chlorination residues include hexachlorobenzene.

* * * * *